United States Patent [19]

Allain et al.

[11] Patent Number: 5,029,590
[45] Date of Patent: Jul. 9, 1991

[54] PORTABLE, LIFE DETECTION MONITOR SYSTEM

[76] Inventors: Joseph L. Allain, 4932 Chantilly Dr., New Orleans, La. 70126; Henry Halperin, 2202 Crest Rd., Baltimore, Md. 21209

[21] Appl. No.: 764,837

[22] Filed: Aug. 9, 1985

[51] Int. Cl.⁵ .............................................. A61B 5/04
[52] U.S. Cl. ..................................... 128/710; 128/731
[58] Field of Search ............... 128/696, 702, 709, 710, 128/711, 902, 640, 670, 671, 695, 700, 731, 734

[56] References Cited

U.S. PATENT DOCUMENTS

| | | | |
|---|---|---|---|
| 2,943,628 | 7/1960 | Howell | 128/640 |
| 3,602,215 | 8/1971 | Parnell | 128/902 |
| 3,662,746 | 5/1972 | Saltzberg et al. | 128/710 |
| 3,757,778 | 9/1973 | Graham | 128/902 |
| 4,261,369 | 4/1981 | Allor | 128/696 |
| 4,606,352 | 8/1986 | Geddes et al. | 128/702 |

Primary Examiner—William E. Kamm
Attorney, Agent, or Firm—Jim Zegeer

[57] ABSTRACT

An electronic, miniaturized, pocket-size device having a multiplicity of tri-electrode sets (note FIGS. 3 and 6A) for monitoring and storing EKG or EEG signals, one being positive and the other negative, with the third being a possible signal opposite to the signal received sent in the opposite direction (to the electrode), lessening background noise. Each is connected to one or more amplifiers joined in a central amplifier which breaks up the signals into two separate, related signals, one being the difference in the bias voltages of the positive and negative voltages and the second being the amplified difference of the signals. The first is sent to a voltage sensitive detector, which sends a signal out when this difference becomes sufficient, the detector being set for triggering when an electrode becomes detached or otherwise defective, as in even an abnormal EKG or EEG the voltages will not be greatly different. The second signal is sent to a filter and then to appropriate detection equipment for monitoring the condition of the EKG or EEG, for example a peak detector, grounded needle meter, analog-to-digital converter, noise indicator, outside jack, etc. The peak detector is connected to an indicator and to the analog-to-digital converter to keep track of when peaks are reached to get a "print out" record of them. A central processor capable of storage or output is used with the analog-to-digital converter to send the signal to a screen or saving it for future reference.

6 Claims, 6 Drawing Sheets

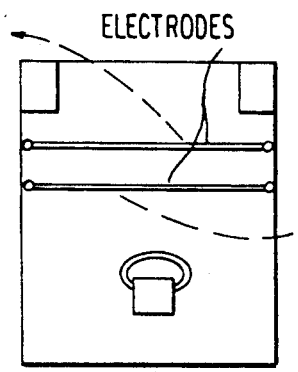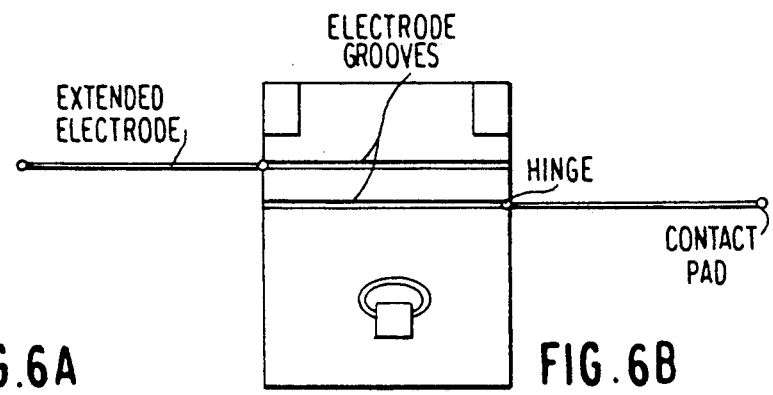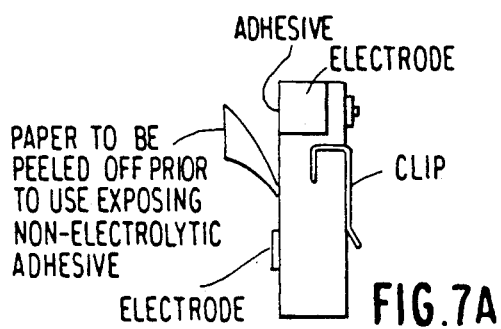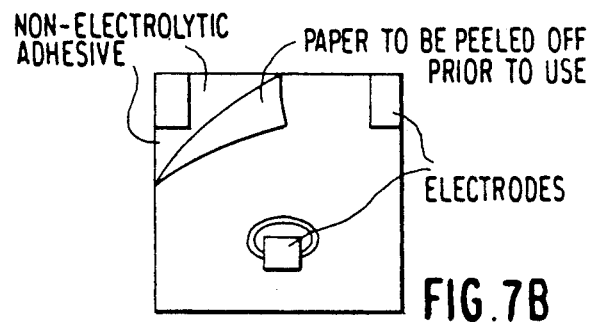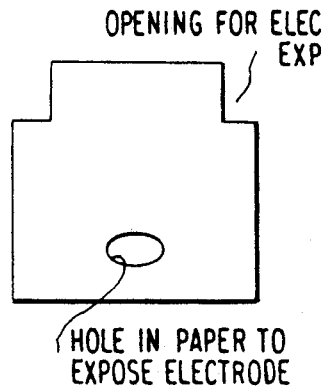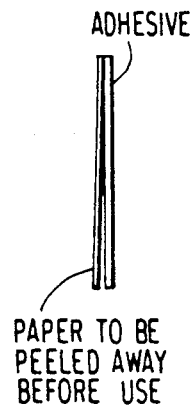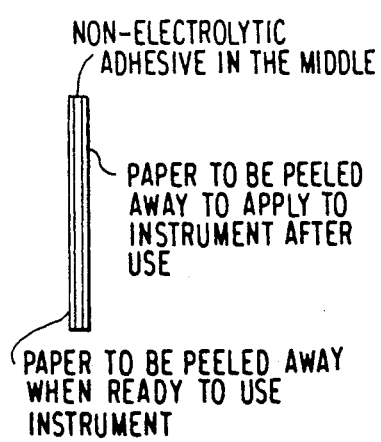

FIG. 12
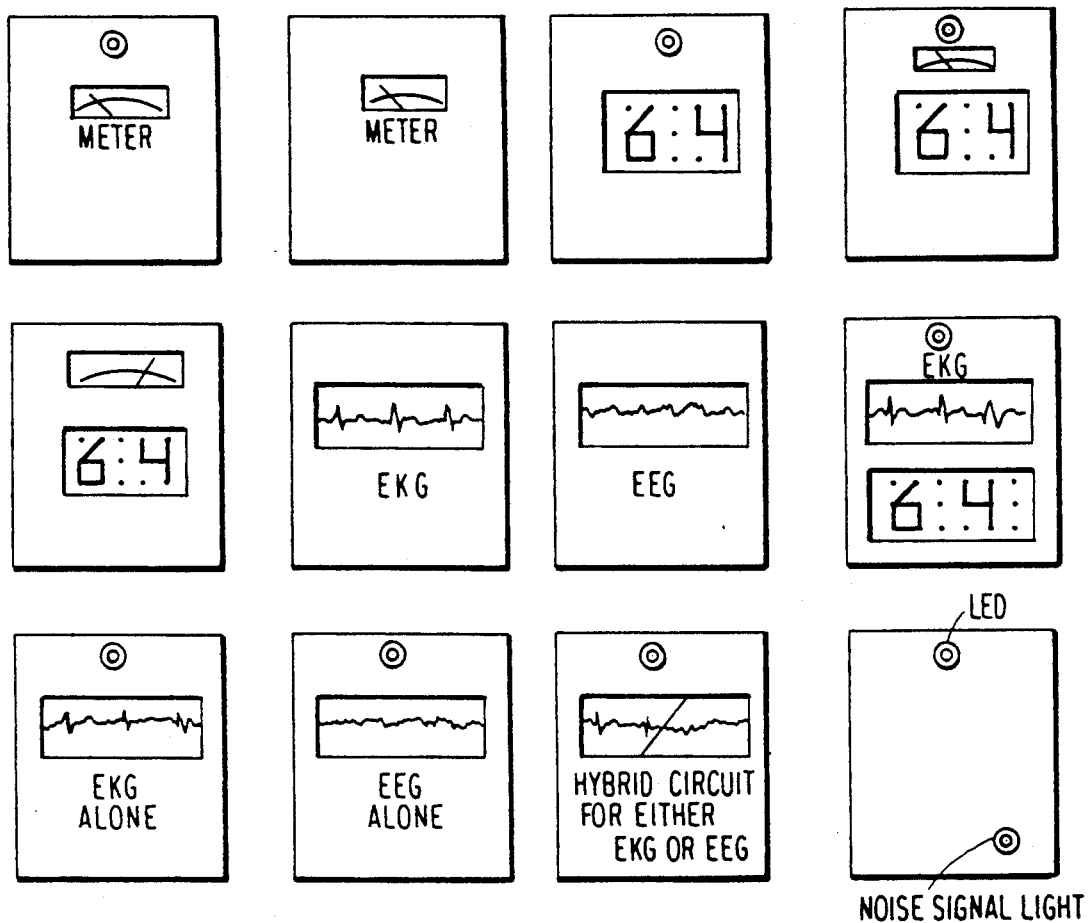
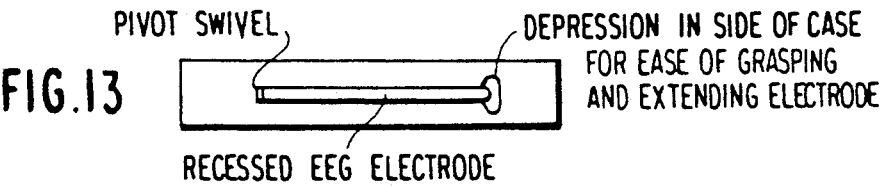
FIG. 13
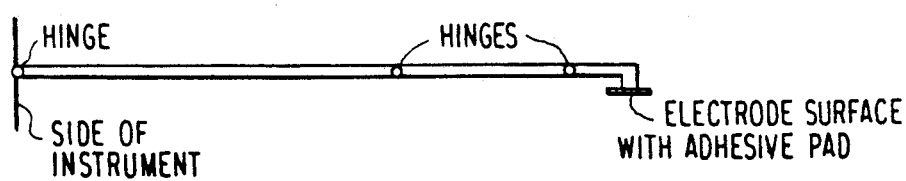
FIG. 14

PORTABLE, LIFE DETECTION MONITOR SYSTEM

REFERENCE TO RELATED APPLICATIONS

This application is directed to improved versions of the "Life Monitor System" of Dr. Allain's prior application Ser. No. 156,056 filed 06/03/80, issued as U.S. Pat. No. 4,350,164, on Sept. 21, 1982.

BACKGROUND of INVENTION

1. Field of Invention

The present invention relates to a portable monitoring device to monitor the internal electrical impulses generated by a live mammal, including humans, and in particular to monitor and produce EKG's and EEG's with a small pocket-size device.

2. Prior Art

Numerous portable electronic devices designed for processing electrical signals from the heart are described in the patent literature. There are many problems with these devices as they are described. All of the devices except for the cathode ray tube device, give as output a flashing light, an audio tone, or a meter deflection. There is no way of knowing whether the light, tone, or meter deflection represents electrical activity or noise.

Anyone familiar with EKG's knows that intermittent lead contact is a problem even with adhesive electrodes, and any device which has to reliably record or detect biopotentials has to have the capability of informing the operator when a lead failure has occurred. High impedance amplifiers as described in some of the patents are helpful, but good contact is still a problem. In conventional EKG's and EEG's poor lead contact is usually obvious by the characteristic noise pattern on the recorded signal. For devices with only a light, audio signal, or meter the cadence is supposed to indicate proper or improper operation; however, the signal and the noise spectrum can be sufficiently close that the device can be "fooled" into indicating a valid signal when indeed none exists. The device can also misinterpret lack of contact as no signal being sent. These lead failure modes can and do occur without any obvious misapplication of the device or electrode.

The cathode ray tube device is too bulky to be accepted as an easily portable device for use in field or on site situations. For example, the device described in U.S. Pat. No. 3,776,228 to Semler (issued 12/73) has a minimum electrode spacing of 7 cm. It also has a fluid reservoir present. This fluid is undersirable because of its bulk and its potential for leaking over both the internal parts of the device, and the person carrying the device. The fluid could also become contaminated with microorganisms that could spread disease from patient to patient. It is common practive to use a sterile interface between the patient and the measuring device (ie, disposable electrodes). This device describes the electrodes as being made out of "highly conductive material such as silver or nickle." These kinds of electrodes are highly subject to polarization potentials, which are manifested as noise currents. A much better kind of electrode is one made out of a combination of silver with silver chloride, which has much less polarization.

It is naive to propose that physicians and paramedics are going to spend an adequate amount of time to learn the characteristic: beeps" of the device described in U.S. Pat. No. 3,830,227 to Green (issued 8/74). In fact, no data is presented to show that any such characteristic beeps occur. There are many different patterns on the EKG that are clinically distinct, but show up as only very subtle changes on the EKG record. Also, since the currently accepted method for determining the electrical activity of the heart consists of interpreting EKG records, it is very doubtful that the devices described would be accepted by the medical community.

The device described in U.S. Pat. No. 3,991,747 to Stanley et al (issued 11/76) requires supplemental processing equipment to be of value. Its other considerations are as noted above.

| U.S. Patent Documents | | |
| --- | --- | --- |
| 2,327,874 | 8/1943 | DeJong |
| 2,983,273 | 5/1961 | Howell |
| 3,085,577 | 4/1963 | Berman et al |
| 3,491,750 | 1/1970 | King |
| 3,533,397 | 10/1970 | Scher |
| 3,614,763 | 10/1971 | Yannuzzi |
| 3,848,582 | 11/1974 | Milani et al |
| 4,033,356 | 7/1977 | Hara |
| 4,350,164 | 9/1982 | Allain |
| Foreign Patent Documents | | |
| 250557 | 3/1966 | Austria |
| 562237 | 1957 | Italy |
| Other Publications | | |
| David et al, "A Low Cost Portable Ventricular . . . discriminator", Med. Inst. vol. 7, No. 4, Sep.-Oct. 1973, pp. 237-239. | | |

U.S. Pat. No. 4,350,164 issued Sept. , 1982 to Dr. Joseph L. Allain, one of the co-inventors hereof, is noted. Even the Allain device of the '164 patent, although a great advance over the prior art, was capable of improvement, both in its over-all range of its capabilities and in some of the mechanical details of its housing, linkages and connections of its preferred embodiments.

Another very important requirement of a life detection monitor is its ability to store an EKG or EEG waveform. It a patient has other than an obvious condition, which is often the case, it is necessary for the physician or paramedic to spend a few minutes analyzing the same strip of data. This is not possible to do with the current devices as they are described.

For medicolegal purposes it is desirable for the device to be able to store a portion of the waveform for later read-out on a permanent record. This situation would occur if a patient were pronounced dead at the scene of an accidnet, or after a heart attack. Unless the telemetry equipment were immediately available, this would not be possible with the current, prior art devices.

Thus important considerations partially or completely missing in the totally portable life detection devices as described in the prior art are as follows:

1) Noise considerations;
2) Validation of the method;
3) Brain wave detection;
4) Stored waveform modes;
5) Freeze modes; and/or
6) Small electrode spacing.

3. Summary Discussion of the Present Invention

Numerous advancements in the state of the art have been incorporated in the life detection monitor of the present invention.

These advancements include those in the circuitry, medical features, storage of data, packaging and improved design of the supplemental swing down or out electrodes.

It is thus a primary object of the present invention to provide life detection (e.g. EKG/EEG) portable, pocket-size monitor that is highly reliable in its operation and of compact, pocket-sixe packaging.

It is a further object to provide such a monitor with many different features and capabilities, including for example data storage as well as preferrably both EEG and EKG capabilities.

It is another object to provide the supplemental, swing out electrodes for enhanced spacing in an improved way.

It is a final, general object to cure the problems detailed above with respect to the prior art.

BRIEF DESCRIPTION of the DRAWINGS

For a further understanding of the nature and objects of the present invention, reference should be had to the following detailed description, taken in conjunction with the accompanying drawings in which like parts are given like reference numerals and wherein:

FIGS. 6A and 6B are rear views of a further embodiment, similar to that of FIG. 2, showing both electrodes in their storage dispositions and in their extended, operative dispositions, respectively.

FIGS. 7A and 7B are side and rear views, respectively, of a further embodiment using a peel-off covering on the rear of the monitor system.

FIG. 8 is a plan back view of a further embodiment of the peel-off covering, similar to that shown in FIG. 7A but with openings provided on the corners and in the center-bottom to expose the electrodes of the life monitor system.

FIG. 9A and 9B are side views of the paper backing of FIG. 8 showing it as it would appear on the instrument with one layer of paper removed and as it would appear before use, respectively.

FIG. 12 is a collection of plan views illustrating twelve exemplary variations in the signal result display side for the life monitor system of the present invention.

FIG. 13 is a side view of a further embodiment of the monitor including a depression in the side of the case at the bottom end of the electrode storage slot for ease of grasping and extending the stored electrode.

FIG. 14 is a side view of the fully extended electrode of FIG. 13 including its three hinges (more being possible), the left most one of which is to the monitor body and the other two (or more) being internal, allowing the electrode to be folded out about itself for a maximum extended, operative length (FIG. 14) and a relatively short storage length (FIG. 13).

DETAILED DESCRIPTION OF THE PREFERRED EXEMPLARY EMBODIMENTS

Figure 1:
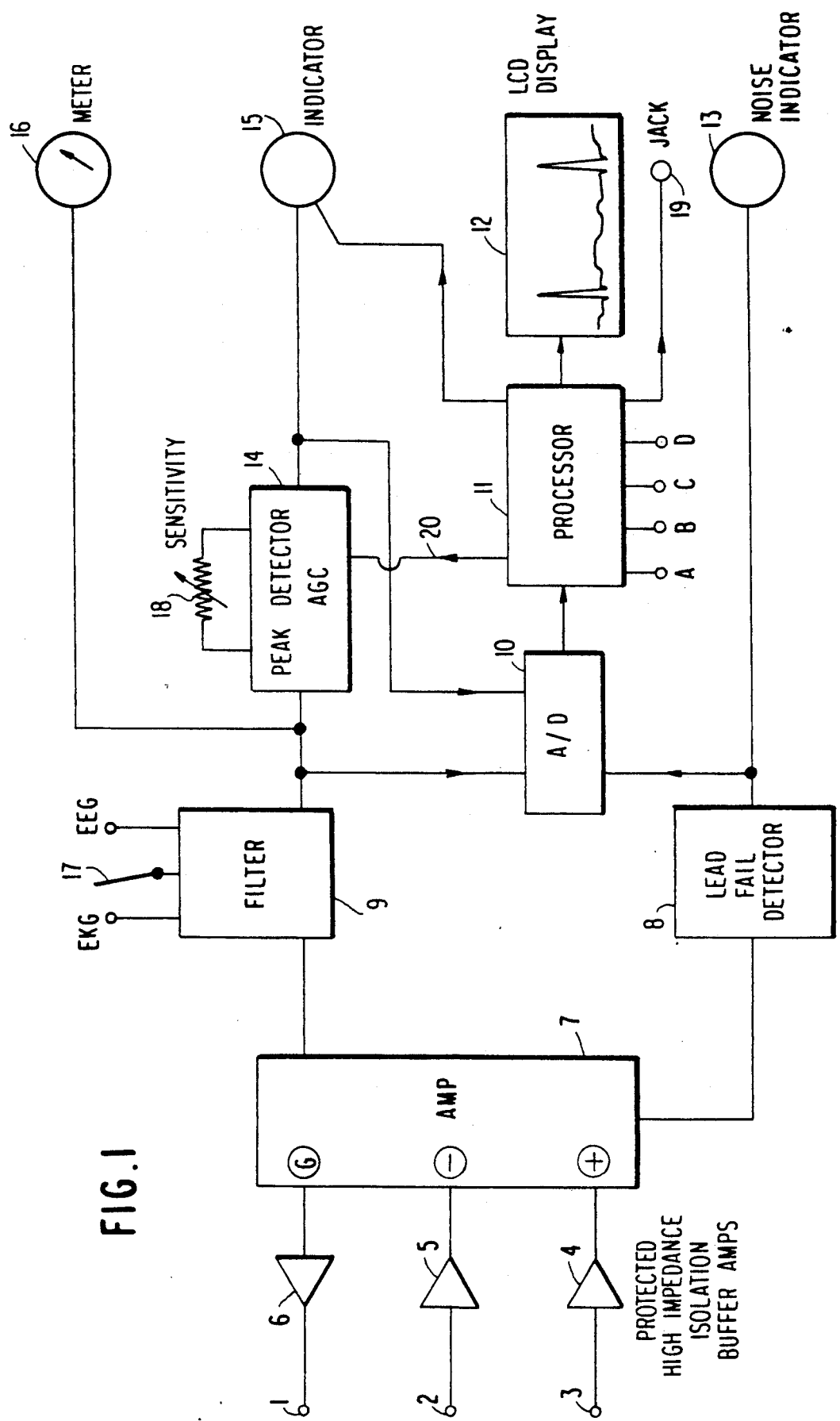
FIG. 1 is a generalized schematic of the preferred, exemplary electronic circuitry used in one of the exemplary embodiments of the portable life detection monitor system of the present invention.

The preferred, exemplary embodiment of the exemplary electronic circuitry for use in the portable, life detection monitor system of the present invention is schematically illustrated in FIG. 1. As can be seen, input to the device is by two (2,3) or three (1,2,3) electrodes in contact with the patient's body, either over the chest area for EKG recordings or over the skull area for EEG recordings. The electrodes can be of the non-polarizing type or of a material having a low polarizing nature, such as for example silver, silver chloride alloy or gold plate.

The minimum spacing of the electrodes can be for example one to two cm because of the high quality of the amplifier elements used, and because of the special noise rejection circuitry. For certain critical EEG recordings, special swing out or telescoping electrodes described more fully below are present to increase the electrode spacing, for better noise rejection. Biopotentials are buffered by protected, high impedance, isolation amplifiers 4, 5. Amplifier 6 is of the same type as amplifiers 4 and 5, but amplifier 6 acts as a DC return for improving common mode reflection.

Amplifier 7 outputs the amplified difference of the signals from amplifiers 4 and 5 to the filter 9. Amplifier 7 also outputs a signal to lead fail detector 8, which is the difference of the bias voltages of amplifiers 4 and 5. When the bias difference is of sufficient magnitude, this indicates that a lead failure has occured. This is indicated as an output to the noise indicator and also as an output to the analog to digital converter 10 for processing by the processor.

The filter 9 is optimized for EKG or EEG signals depending on which position the selector switch 17 is placed. Output from the filter 9 goes to the peak detector 14 which has variable sensitivity control 18. The sensitivity control can be replaced fully or in part by an AGC circuit. The sensitivity can also be controlled by the processor 11, depending on the noise output from the lead fail detector 8 and the peak detector 14. Output from the filter 9 can also go to a meter of the galvanic or solid state type.

The processor 11 receives inputs via the analog to digital converter 10 from the filter 9, the peak detector 14, and the lead fail detector 8. It has as output a signal to the peak detector to adjust its sensitivity, thereby implementing a hardware peak detector.

The peak detector can also be implemented in software in the processor 11 by many standard techniques. The processor can output to the indicator 15 to show the presence of the electrical activity in the absence of noise. It can also output to the LCD display 12.

Waveforms can be displayed on the LCD display. Messages can also be displayed such as the rate of heartbeat, or the condition of the leads. The waveform on the display can be frozen by pushing the appropriate switch on the processor for later read-out to a permanent record via jack 19. It is, of course, within the scope of this invention to have a small printer available as an integrated part of the monitor.

It must be noted that the above discussion is only one embodiment of the electrical and electronic aspects of the invention. The processor and analog to digital converter can be left out with the output from filter 9 going directly to the LCD display 12. In this case the feedback 20 from the processor to the peak detector would not be present, and the peak detector 14 would be adjusted by automatic gain control (AGC) circuitry in it or by the sensitivity control 18.

The foregoing described circuitry is a significant improvement over the state of the art, even if the A/D, processor, and LCD were not present. In this version the output would be to indicators 13 and 15, and possibly to meter 16. The improvement of the present invention include the form of selective filtering, noise/lead fail detection, electrode spacing, and electrode makeup.

All of the above versions of the device are packaged in a small, lightweight case suitable for carrying in one's pocket or bag. The monitor device uses low power circuitry and is battery operated. The processor and LCD display have the capability of storing information, and retaining it when the power to the device is turned off, including the storage of one or more reference displays which may be visually compared by the operator, by alternate or simultaneous visual display or electronically compared by the processor.

Figure 2:
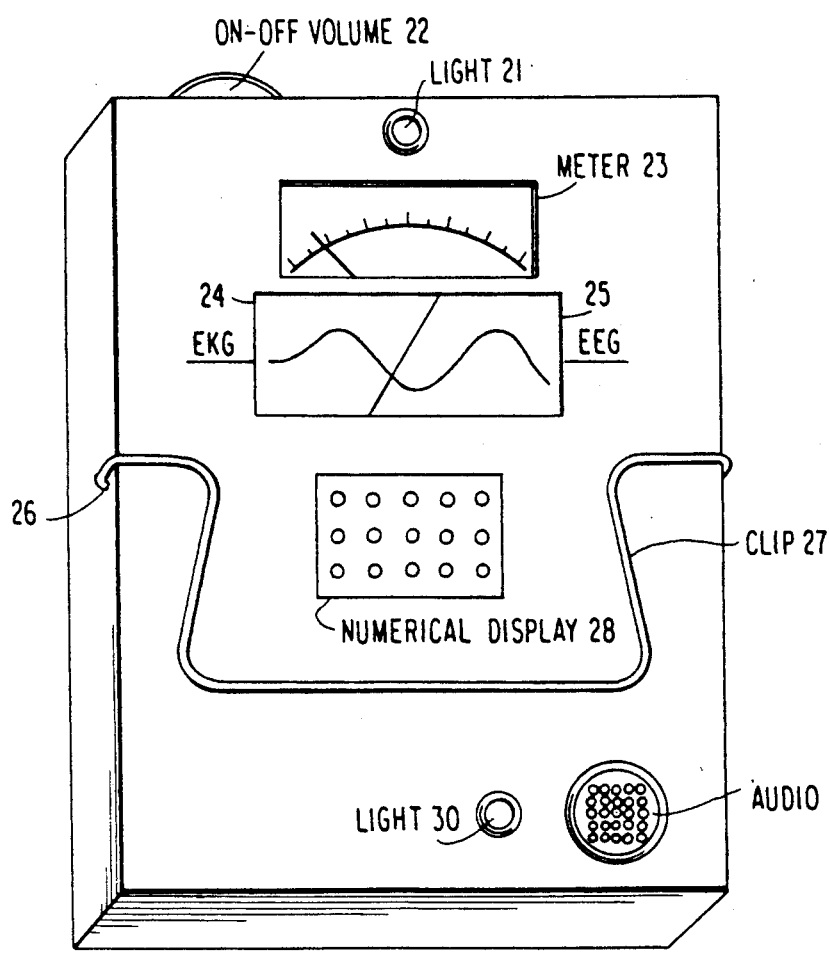
FIG. 2 is a front, perspective view of a first preferred, exemplary embodiment of the monitor of the present invention.

Referring to FIG. 2, it can be seen that several different displays are possible to allow the user an optimum monitoring of the patient. An on-off and volume dial 22 is located at the top of the device so as to allow a proper adjustment of the output of the voltage amplifiers 4–7. Additionally, a switch, not shown, may be provided for adjusting the filter 9.

For monitoring the patient, there is provided a light 21 following the pulses from electrodes 1–3. Additionally, a meter 23 is provided for monitoring the strength of the signals. A numerical display 28 may replace or supplement the meter or may display a high or low of the metered output.

A visual analog display 24 may be made of the EKG or EEG or both. This visual display may include the comparison of a reference signal from the processor 11.

An audio 29 and light 30 display may be added in line with the lead fail detector 8 of FIG. 1 to determine when the signal is being affected by outside interference or noise or upon a failure of the signal referred to as noise indicator 13 in FIG. 1, discussed above.

Because of the compact size of the unit, it may fit in either a coat or even a shirt pocket. In such a case, a removable clip 27 may be attached by attachments 26 to the carrying case holding the displays for clipping the device to the user's clothing.

Figure 3:
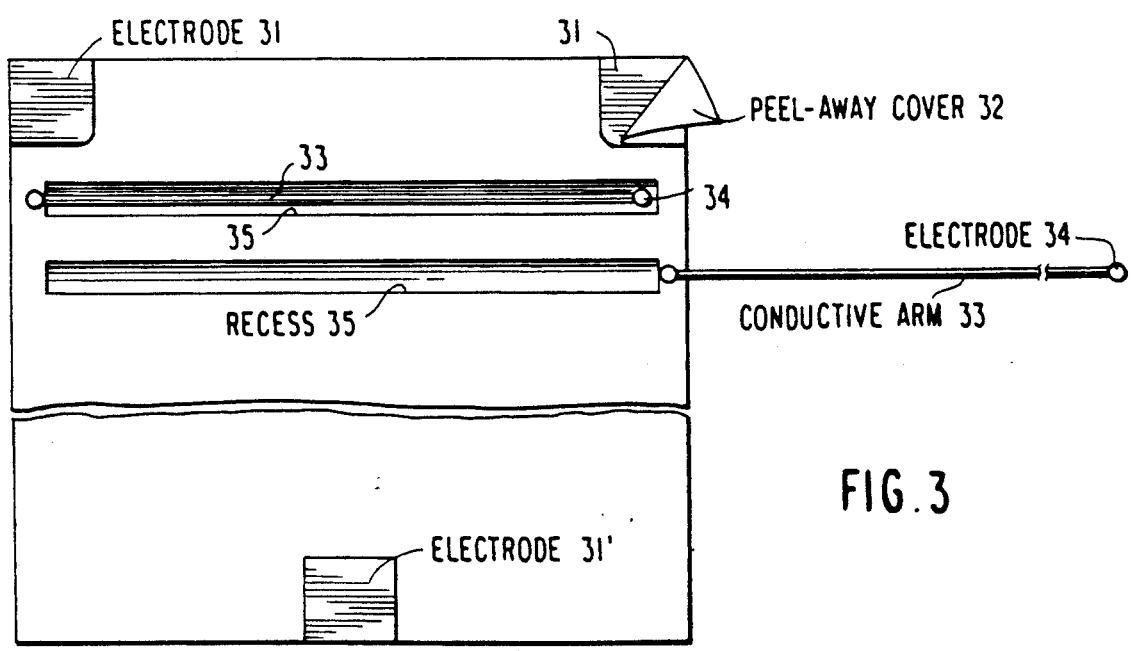
FIG. 3 is a rear view of the exemplary embodiment of FIG. 2 with the upper one of the electrodes in its storage disposition and the lower one swung out into its operative disposition.

FIG. 3 shows a view of the rear of the device showing two alternate sets of electrodes. Electrodes 31 may be placed at different corners of the device with a third electrode 31' located at the center, bottom of the device, forming a triangulated set of fixed electrodes. Although the illustrated spacing and location is preferred for maximum separation distance for the electrode, the three electrodes 31, 31' could be more closely spaced and centrally located, if desired.

These electrodes may be covered by condctive adhesive, which is in turn covered by peel away covers 32, so that the device may be attached to the patient by the adhesives to prevent false signals due to any unsteadiness on the part of the user. Additional adhesives may be provided, if desired, to further hold the body of the instrument to the patient.

Figure 4:
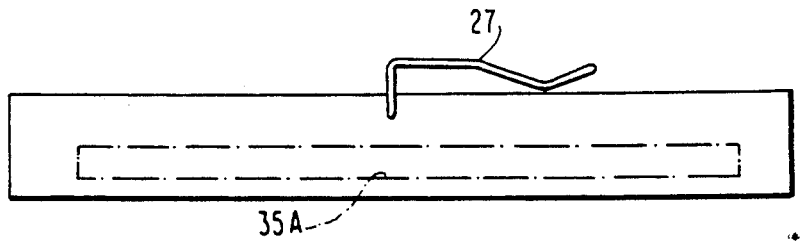
FIG. 4 is a side view of the embodiment of FIG. 2 showing an alternate location in phantom line for the location of the supplemental swing-out electrodes.
Figure 5:
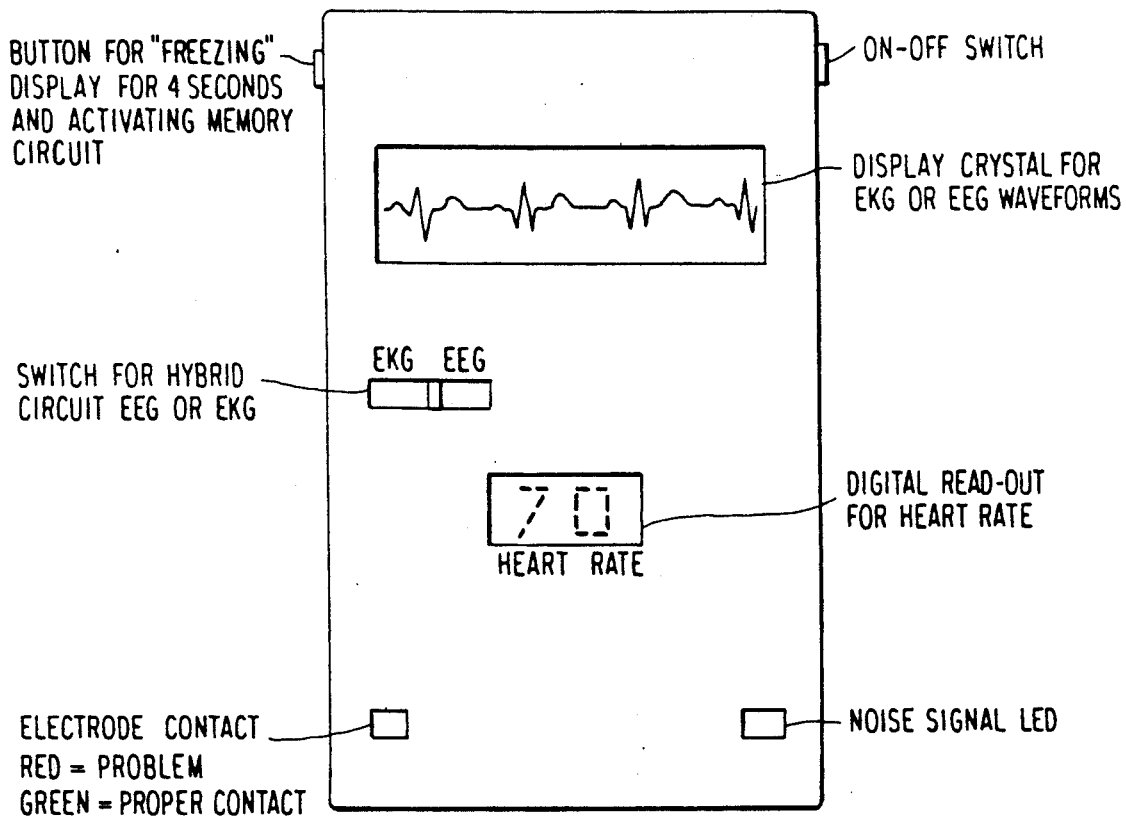
FIG. 5 is a front view of a second, preferred, exemplary embodiment of the present invention with the back and side views being the same as that of FIGS. 3 and 4, with the exception that the clip 27 is not used and the side location 35A is preferred for the electrodes of the embodiment of FIG. 5.

Supplemental, swing out electrodes 34 are mounted on electrically conductive arms 33, which fit into recesses 35 in the back of the case of the device. In this way, the distance for spacing the electrodes may be increased to for example ten cm. without changing the compact nature of the device. Alternatively, these electrodes may be mounted as swing out electrodes mounted within recesses 35A (note phantom lined box in FIG. 4) on the sides of the device, or, alternatively, telescoping electrodes or other variable effective length electrode structures could be used, other variations being suggested in the allain '164 patent referred to above. As a further example, the supplemental electrodes may be mounted on flexible cords which may be stored inside an appropriate storage chamber in the device.

Figure 10:
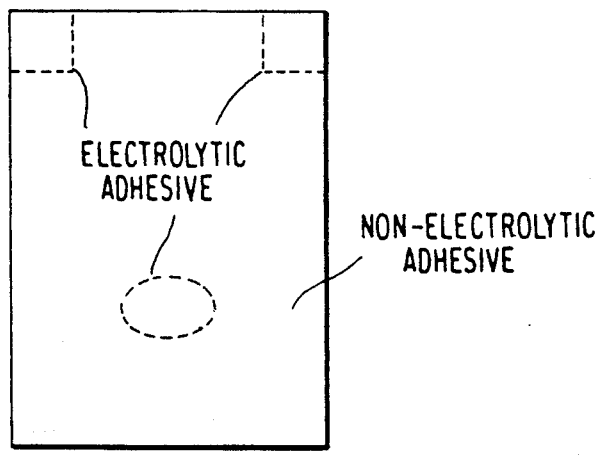
FIG. 10 is a plan view of a further embodiment of the paper backing, similar to that of FIG. 8, but having corresponding areas of electrolytic or electrically conductive adhesive areas in place of the electrode openings of the embodiment of FIG. 8.
Figure 11A:
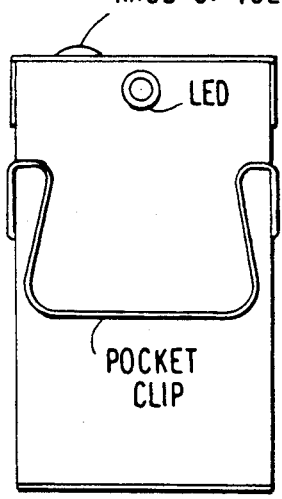
FIGS. 11A-11E are front, back, side, top and bottom views of a still further embodiment of the life monitor system of the present invention.
Figure 11B:
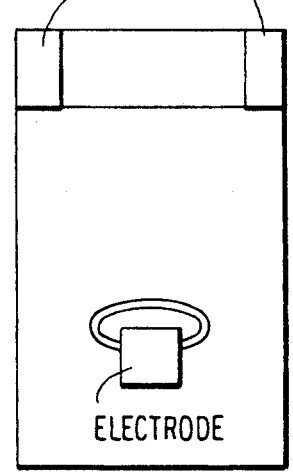
Figure 11C:
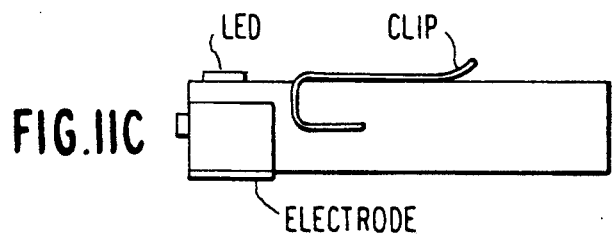
Figure 11D:
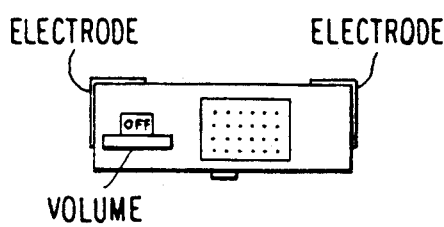
Figure 11E:
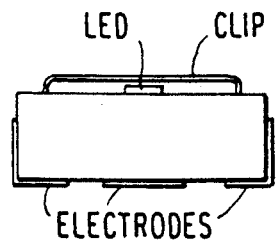

Other alternate, exemplary embodiments of the monitor device of the present invention are illustrated in the additional FIGS. 5–14. The instrument shown in FIG. 5 should be carried in a soft leather case, which could be provided with clip-on capabilities for ease of carrying. FIG. 6A is a rear view with the electrode folded in grooves and FIG. 6B is a rear view showing the electrodes extended. All meters may have a "noise" light connected to allow the observer to know when artifacts are mixed with signal or comprise the entire signal. FIGS. 7A, 7B, 8 and 9A and 9B relate to non-conductive adhesive covering non-electrode portions of the back of the instrument to be exposed by peeling-off paper covering when ready to use and pressing onto chest or forehead so that trembling artifacts of hands may be removed. FIG. 8 is a back view of the paper covering before application to the instrument, FIG. 9A is a side view of the paper backing on the instrument and FIG. 9B is a side view of the paper backing before use. FIG. 10 is a front view of paper backing with electrolytic adhesive over the electrodes and non-electrolytic adhesive over the remainder of the back of the instrument. In this view, the paper is exposed prior to application to instrument for actual use. FIGS. 11A, 11B, 11C, 11D and 11E are front, back, side, top and bottom views, respectively, of a further embodiment of the invention. FIG. 12 are front plan views of the display side of the instrument with exemplary variations in the display. A light switch may be provided on the front of the monitor which should light when the on-off switch is depressed to determine if battery and all circuit components are functioning properly before use of the instrument. As shown in FIGS. 13 and 14, the swing-out EEG electrodes should preferably be recessed in the side of the instrument and be hinged to allow for proper contact with various forehead configurations. It is further noted that the hybrid circuit of the preferred embodiment could be separated, and the EEG and EKG functions separately incorporated into different, separate instruments for separate or conjunctive use, as desired.

Because many varying and different embodiments may be made within the scope of the inventive concept herein taught, and because many modifications may be made in the embodiment(s) herein detailed in accordance with the descriptive requirements of the law, it is to be understood that the details herein are to be interpreted as illustrative and not in a limiting sense.

What is claimed is:

1. In a portable life detection monitor system having a plurality of electrodes for attachment to a human body for monitoring electrical potentials generated by said body between selected points thereon, circuit means for processing said electrical signals, and a utilization device connected to said circuit means, the improvement wherein said circuit means includes
   an electrical filter connected to receive signals from said electrodes, switch means connected to said electrical filter to selectively optimize the output of said filter according to whether a said plurality of electrodes are (1) on the skull of said human body to monitor EEG signals or (2) on the chest of said human body to monitor EKG signals.

2. The portable life detection monitor system defined in claim 1 wherein said monitor system include lead fail detector means for detecting the failure of one or more of said electrodes and, means for indicating an output from said lead fail detector means.

3. The portable life detection monitor defined in claim 1 including a peak detector connected to said filter and indicator means connected to said peak detector.

4. The portable life detection monitor defined in claim 1 including an analog-to-digital converter connected to said filter, a microprocessor connected to said analog-to-digital converter, and a liquid crystal display connected to said microprocessor to display the waveform signals produced by said electrodes.

5. The portable life detection monitor defined in claim 1 wherein said plurality of electrodes includes first and second electrodes and first and second high impedance amplifiers having their respective inputs connected to said first and second electrodes, respectively, and circuit means connected to receive the outputs of said first and second high impedance amplifiers and produce a difference signal, and means for utilizing said difference signal.

6. In a portable life monitor system having a plurality of electrodes for attachment to selected positions on a human body to detect electrical signals generated by said human body, circuit means for processing said electrical signals and utilization means connected to said circuit means, the improvement comprising,
   said circuit means including:
   means for producing a difference signal corresponding to the difference of signals from a selected pair of said electrodes,
   filter means connected to optimize said difference signal, means for modifying said filter according to the useful signal related to the position of said electrodes on the human body,
   analog-to-digital converter means for digitizing said difference signal,
   microprocessor means connected to said analog-to-digital converter and programmed to analyze said difference signal, and
   said utilization means including:
   display means connected to said microprocessor for displaying the waveform of said difference signal.

* * * * *